United States Patent [19]
Hahnen et al.

[11] Patent Number: 5,389,104
[45] Date of Patent: Feb. 14, 1995

[54] ARTHROSCOPIC SURGICAL INSTRUMENTS

[75] Inventors: Kevin F. Hahnen, Ft. Lauderdale; Gustavo Aguirre, Miami; Peter Kratsch, Sunrise, all of Fla.

[73] Assignee: Symbiosis Corporation, Miami, Fla.

[21] Appl. No.: 101,190

[22] Filed: Aug. 3, 1993

Related U.S. Application Data

[63] Continuation-in-part of Ser. No. 978,249, Nov. 18, 1992.

[51] Int. Cl.$^6$ ............................................. A61B 17/32
[52] U.S. Cl. ........................................ 606/174; 606/37
[58] Field of Search ............... 606/79, 83, 167, 174, 606/175, 184, 37, 39, 207; 188/376; 128/751; 604/22

[56] References Cited

U.S. PATENT DOCUMENTS

| | | | |
|---|---|---|---|
| 1,754,806 | 4/1930 | Stevenson . | |
| 3,504,460 | 4/1970 | Solberg | 52/98 |
| 4,522,206 | 6/1985 | Whipple et al. . | |
| 4,712,545 | 12/1987 | Honkanen . | |
| 4,896,678 | 1/1990 | Ogawa | 128/751 |
| 4,953,559 | 9/1990 | Salerno | 606/39 |
| 4,994,024 | 2/1991 | Falk | 604/22 |
| 5,147,356 | 9/1992 | Bhatta | 606/37 |
| 5,152,780 | 10/1992 | Honkanen et al. | 606/205 |
| 5,219,357 | 6/1993 | Honkanen et al. | 606/205 |

Primary Examiner—Tamara L. Graysay
Attorney, Agent, or Firm—David P. Gordon

[57] ABSTRACT

An arthroscopic surgical instrument includes a hollow tube with an actuator coupled to its proximal end and an end effector coupled to its distal end. The actuator and the end effector are coupled by a cylindrical push rod which passes through the hollow tube. The push rod includes a frangible link in the form of a flattened portion with strength reducing semicircular side cuts which breaks when a predetermined force is applied to the end effector by the actuator. The end effector includes a stationary jaw and a movable jaw. The stationary jaw is coupled to the distal end of the tube and receives the push rod. The movable jaw is coupled to push rod and is pivotally coupled to the stationary jaw by arcuate engaging surfaces on both jaws. The movable jaw is also provided with a pair of serrated knife-like edges with an inner concave surface between them and the stationary jaw is provided with a receiving opening into which the movable jaw fits when the jaws are in a closed position. The receiving opening is defined by a pair of side walls having an upper taper which terminates in a sharp edge and a distal end wall having a concave inner surface. The concavity of the inner surface of the end wall is defined by a radius from the axis of rotation of the movable jaw. An electrical connection to the hollow tube is provided for supplying the jaws with a cautery current.

22 Claims, 6 Drawing Sheets

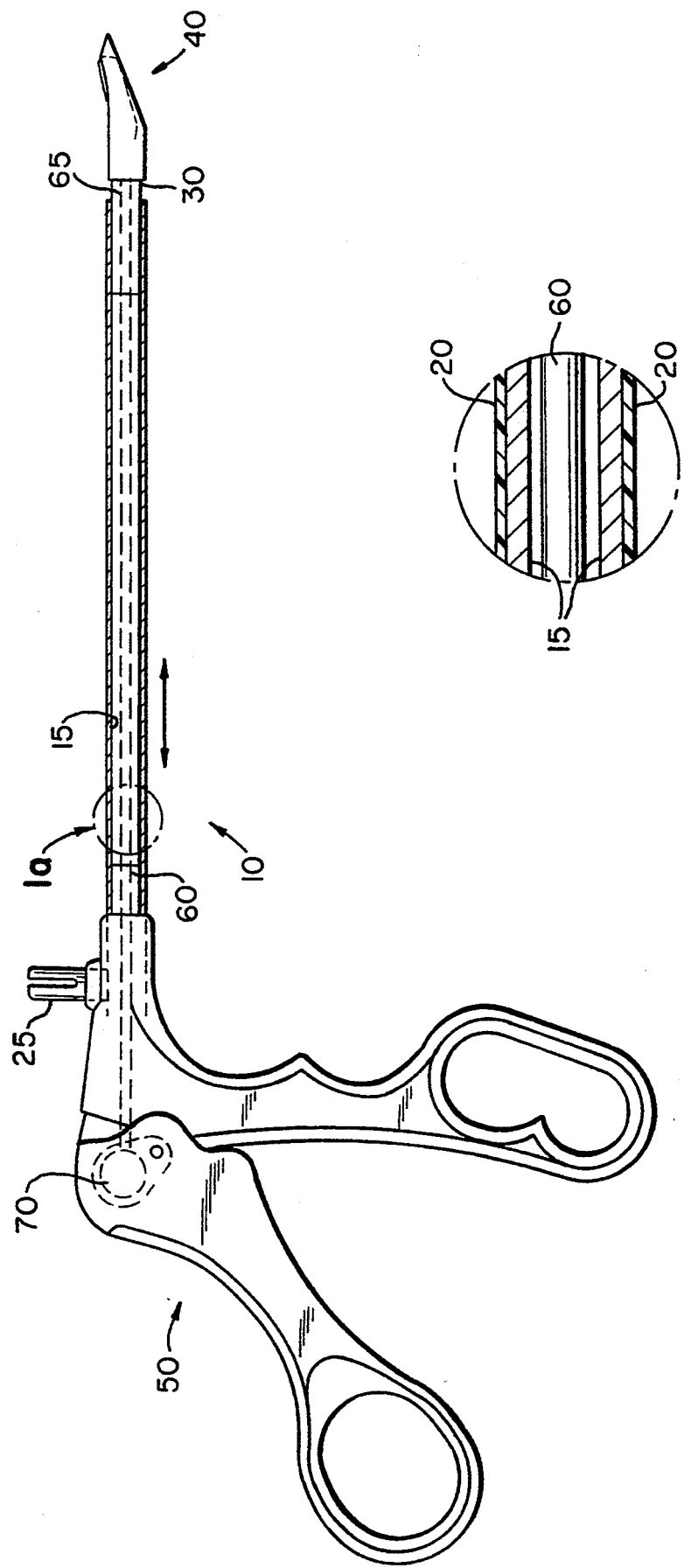

ARTHROSCOPIC SURGICAL INSTRUMENTS

This application is a continuation-in-part of copending application Ser. No. 07/978,249, filed Nov. 18, 1992, pending.

BACKGROUND OF THE INVENTION

1. Field of the Invention

The present invention broadly relates to arthroscopic surgical instruments. More particularly, the invention relates to arthroscopic surgical instruments which are preferably disposable and which include push rods with a failure mechanism for excess force, and end effectors with desired arrangements.

2. State of the Art

The arthroscopy procedure has become a widely practiced surgical procedure. Arthroscopy involves making one or more relatively small incisions in order to examine the interior of a joint with an endoscope and to perform surgical operations on the joint. Typically, the surgical procedure involves inserting a cutter, dissector, or other surgical instrument through at least one incision for purposes of manipulating and/or cutting the bone, meniscus, tissue, and cartilage comprising the joint.

The disposable arthroscopic tools of the prior art are somewhat similar to other endoscopic tools used in endoscopic procedures involving softer tissues and organs. These tools, such as laparoscopy tools, generally include a tube, a push rod which extends through the tube, an actuating means engaging the tube and the push rod for imparting reciprocal axial motion to the push rod, end effector means coupled to the push rod, and a clevis coupled to the tube at its proximal end and to the end effector means at its distal end, wherein axial movement of the push rod effects movement of the end effector means in a plane parallel to the longitudinal axis of the push rod. The end effector means of the art can take any of many forms, such as, e.g., a scissors, a dissector, or a grasper. Additionally, the end effector means can be double acting or single acting.

Since there is a limit as to how strong the tools of the art can be made and still be small enough for use in arthroscopy, there is always the possibility that the tool will break while in use. Indeed, this problem is compounded with disposable tools, typically made from weaker materials than the standard stainless steel of non-disposable tools. While this is a remote possibility in most endoscopic procedures involving soft or relatively soft tissues, when used in arthroscopic procedures involving bone tissue, the possibility that an end effector or distal linkage member will break is increased since additional force must be applied to the end effectors through the actuating means in order to grasp or cut the bone tissue. In such a case, if a portion of the end effector or distal linkage breaks, it may become lodged in the joint and will require additional procedures to remove it.

In the field of endoscopy, U.S. Pat. No. 4,896,678 to Ogawa partially addresses this problem. In Ogawa, means are provided for releasing the transmission of force to the end effectors when the operating force exceeds a predetermined amount. One mechanism used by Ogawa to release the force is a V-shaped notch in the push rod which is intended to fail upon the application of excessive force. The teachings of Ogawa, however, have not been applied to arthroscopic instruments in the past.

Improvements have been made in end effectors for use in arthroscopy. In particular, durable surgical forceps and punch end effectors are disclosed in U.S. Pat. No. 4,712,545 to Honkanen. Honkanen's end effectors comprise a stationary jaw and a movable jaw wherein the movable jaw is attached to the stationary jaw by a first arcuate lug and groove arrangement and to a push rod by a second arcuate lug and groove arrangement. The push rod moves relative to the stationary jaw and engages the movable jaw by the second lug and groove arrangement so that the movable jaw is forced to slide by the first lug and groove arrangement relative to the stationary jaw to open or close. The jaws are configured in different ways to act as a punch or a forceps. This arrangement relieves much of the stress associated with the pivot point on end effectors, but is a relatively complex construction, particularly with regard to the second arcuate lug and groove arrangement.

Other strength enhancing improvements in end effectors are disclosed in U.S. Pat. No. 5,152,780 to Honkanen et al. which describes a stationary jaw having an integral clevis pin and a movable jaw having an arcuate engaging groove coupled to a push rod having a stud. The stationary jaw is generally U-shaped member with a hourglass shaped integral pivot pin. The movable jaw has a slot which seats on the pivot pin. Engagement of the push rod stud with the groove on the movable jaw holds the movable jaw against the pivot pin and rotates the movable jaw about the pivot pin.

Despite the many improvements in arthroscopic instruments in recent years, there are still several disadvantages which need to be overcome. Most arthroscopic end effectors comprise a generally U-shaped stationary member with a movable inner punch member having a serrated surface. A disadvantage of this construction is that force applied to the end effector is distributed over the entire tissue grasped within the U-shaped member. This limits the efficiency of the cutting action of the punch. In addition, the serrated surface sometimes pushes the tissue out of the U-shaped member before it can be cut. Moreover, while certain improvements have been made in frangible links to prevent end effector breakage, some of these links are difficult to manufacture. In addition, while it is known to supply certain endoscopic instruments with a cautery current, arthroscopic instruments have never before been provided with cautery capability.

SUMMARY OF THE INVENTION

It is therefore an object of the invention to provide an arthroscopic tool having end effectors which provide a superior cutting/punching action.

It is another object of the invention to provide an arthroscopic tool having end effectors which assume a surgical punch configuration but which are scissor-like in their cutting action.

It is an additional object of the invention to provide an arthroscopic tool having an actuating means, a push rod, and a distal linkage connected to an end effector wherein the end effector and the distal linkage are protected from breakage while the tool is in use.

It is a further object of the invention to provide a disposable arthroscopic tool with a force limiting push rod which may be used with a plurality of different types of end effectors.

It is also an object of the invention to provide an end effector particularly suited for arthroscopy which is particularly durable and able to withstand significant stress.

Another object of the invention is to provide an arthroscopic tool having cautery capability.

In accord with these objects which will be discussed in detail below, the arthroscopic tool of the present invention includes a tube, a push rod which extends through the tube, an actuating means engaging the tube and the push rod for imparting reciprocal axial motion to the push rod, a first stationary end effector coupled to the tube and having a sharp edge defining opening, and a second movable end effector coupled to the push rod and having sharp edges joined by a concave surface, wherein axial movement of the push rod effects movement and rotation of the second movable end effector within the opening of the first stationary end effector, thereby causing a cutting action between the sharp edges of the first and second end effectors. Preferred aspects of the end effectors include: providing the sharp edges of the movable end effector with serrations which form teeth; arranging the serrated edges of the movable end effector such that the points of the teeth contact the sharp edge of the fixed end effector prior to locations directly proximal the teeth points, thereby causing tissue to be pulled in the proximal direction while cutting; providing the stationary end effector with a nose which is distal the opening, where the nose has a concave surface having an arc whose center is at the pivot point of the movable end effector; tapering the cross-sectional thickness of the opening-defining walls of the stationary end effector so as to create the sharp edge; and coupling the fixed and movable end effectors by a flange and groove arrangement. With the preferred end effector arrangement, a superior cutting-/punching action is obtained.

Other aspects of the invention include providing the arthroscopic instrument with a cautery function, and providing the arthroscopic instrument with a frangible link which prevents breakage of the end effector and/or the distal link which links the push rod to the movable end effector. The cautery function is accomplished by covering the stainless steel or aluminum tube on its outer surface with an insulating plastic shrink wrap, forming the actuating means from an insulating material (such as fiber filled polysulfone), and providing an electrical connector which extends through the actuating means to the tube so that cautery current may be supplied to the tube. The frangible link is formed in the push rod by flattening a piece of the otherwise cylindrical push rod, and providing a pair of strength reducing substantially semicircular side cuts. In this manner, the push rod will break under a force less than the force necessary to break the end effector and/or the distal linkage. The push rod and frangible link are preferably made of stainless steel age hardened to a predetermined tensile strength.

The end effectors of the arthroscopic instrument of the present invention are preferably made of an investment cast cobalt alloy or bronze. With the provided materials, the arthroscopic tool is autoclavable, although because of the provided design which limits cost of manufacture, it may also be used as a disposable device.

Additional objects and advantages of the invention will become apparent to those skilled in the art upon reference to the detailed description taken in conjunction with the provided Figures.

BRIEF DESCRIPTION OF THE DRAWINGS

FIG. 1 is a side elevation view, partly in section, of the arthroscopic instrument of the invention;

FIG. 1a is a detail of a portion of the instrument shown in FIG. 1;

FIG. 3c is a cross sectional view along line 3C—3C in FIG. 3a;

FIG. 4b is a cross sectional view along line 4B—4B in FIG. 4a;

DETAILED DESCRIPTION OF THE PREFERRED EMBODIMENTS

Figure 2A:
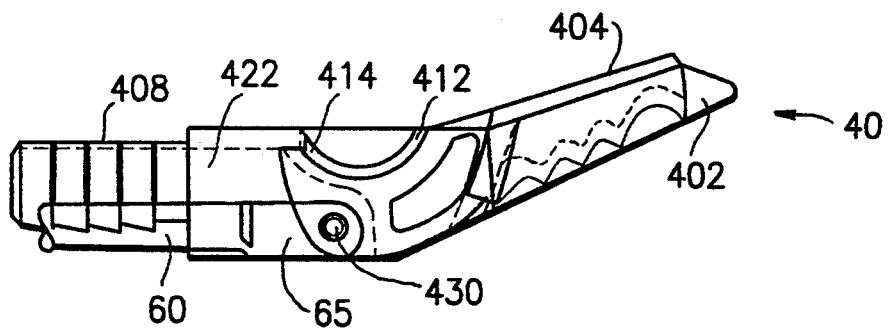
FIG. 2a is a transparent side view of the end effector jaws in the closed position.

With reference to FIGS. 1 and 1a, an arthroscopic surgical instrument is indicated at 10. The arthroscopic surgical instrument 10 broadly comprises an aluminum or stainless steel tube 15, end effectors 40, actuating means 50, and a push rod 60. In accord with one preferred aspect of the invention, the tube 15 is surrounded by a peripheral insulating shrink wrap layer of plastic or ceramic 20, the actuating means is a lever formed from a plastic or other insulating material such as fiber filled polysulfone, and a cautery contact 25 is provided and extends through the insulating actuating means 50 and contacts the tube 15. As shown, the shrink wrap extends from the actuating means 50 to the distal end of tube 15 and preferably over a portion of the end effectors 40 as described in more detail below. If desired, a ferrule (not shown) such as shown and described in U.S. Pat. No. 5,275,612 which is hereby incorporated by reference herein in its entirety can be used to guarantee the continuity of insulation between the shrink wrap 20 and the actuating means 50. In fact, if desired, the coupling of tube 15 and push rod 60 to the actuation means 50 could be enhanced and made rotatable through the use of a rotating ferrule as described in coassigned U.S. Pat. No.

5,174,300, with the cautery contact 25 being able to make contact with the rotating tube 15. Regardless, it will be appreciated that the insulating shrink wrap 20 and other insulating mechanisms guarantee that the only externally "hot" (i.e., receiving cautery voltage) portion of the arthroscopic surgical instrument are the end effectors 40 which receive the cautery voltage from a cautery source (not shown) via the proximal contact 25 and tube 15.

The end effectors 40 of the arthroscopic instrument 10 are preferably formed of an investment cast cobalt alloy or bronze as disclosed in copending U.S. patent Ser. No. 07/837,046, and U.S. Pat. No. 5,234,453 which are incorporated by reference herein. The push rod 60, which in this instrument is formed of stainless steel, is engaged at its distal end 65 to the end effectors 40 through linkage 30, as more fully described below, and is connected at 70 at its proximal end to the manually operable actuating means 50. For purposes herein, the "distal end" of the instrument 10 or any part thereof, is the end closest to the surgical site and distant from the surgeon, while the "proximal end" of the instrument 10 or any part thereof, is the end most proximate the surgeon and distant the surgical site.

In use, the arthroscopy instrument 10 is inserted into a joint area and the actuating means 50 are operated to impart reciprocal motion to the push rod 60. This motion of the push rod 60 is translated to movement of at least one of the end effectors 40 as described more fully below.

Figure 2B:
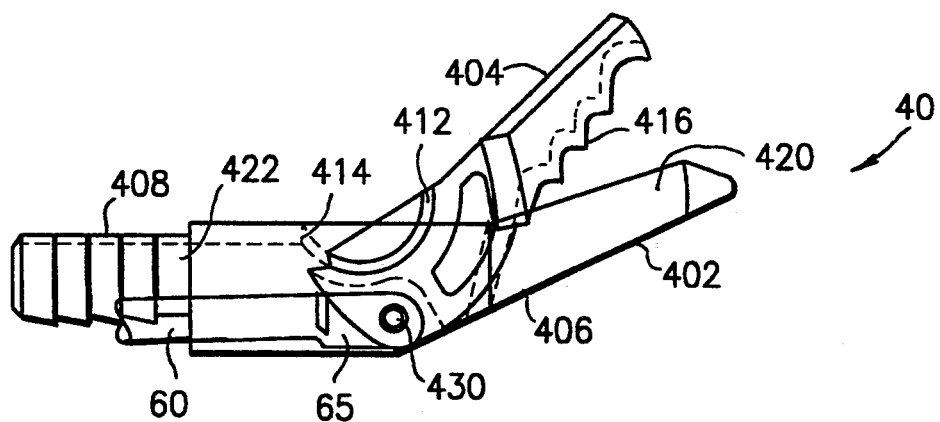
FIG. 2b is a transparent side view of the end effector jaws in the opened position.
Figure 2C:
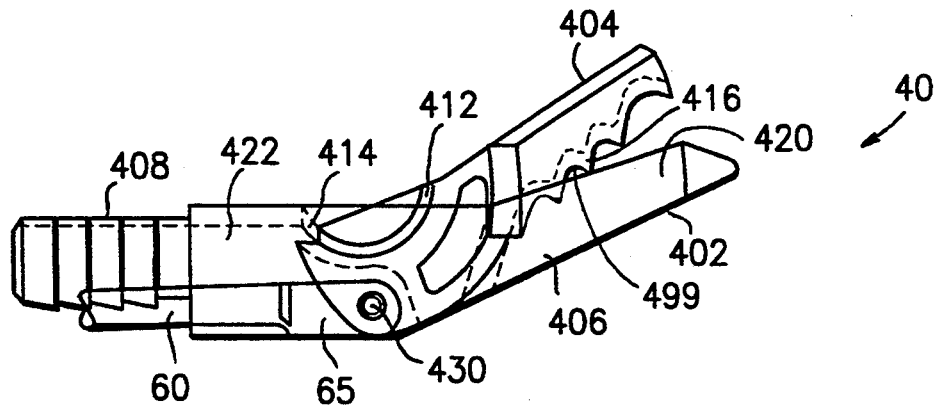
FIG. 2c is a transparent side view of the end effector jaws in a partially open position.

FIGS. 2a, 2b, and 2c show surgical punch end effectors 40 particularly suited for arthroscopy. The end effectors 40 comprise a stationary jaw (end effector) 402 and a movable jaw (end effector) 404. The stationary jaw has a shank portion 408 and a distal portion 406. The shank portion fits lockingly inside tube 15, either by press fit, soldering, or otherwise, and is provided with a throughbore 422 for receiving push rod 60. The movable jaw 404 is pivotally attached to stationary jaw 402 by mating surfaces 412, 414, described more fully below and is linked to the distal end 65 of push rod 60 by a pin 430. The distal portion 406 of the stationary jaw 402 is provided with a sharp edge defining opening 420 (shown in more detail in FIGS. 3a–3c and 3h–3i) into which the movable jaw pivots as shown in FIG. 2a. In this way, the stationary jaw 402 functions as a die and the movable jaw 404 functions as a punch for cutting through bone or joint tissue. To further expedite this function, the movable jaw 404 is provided with knife-like edges 416. Movement of the push rod 60 causes movable jaw 404 to pivot relative to stationary jaw 402 to an open position as shown in FIG. 2b or a closed position as shown in FIG. 2a.

Figure 3A:
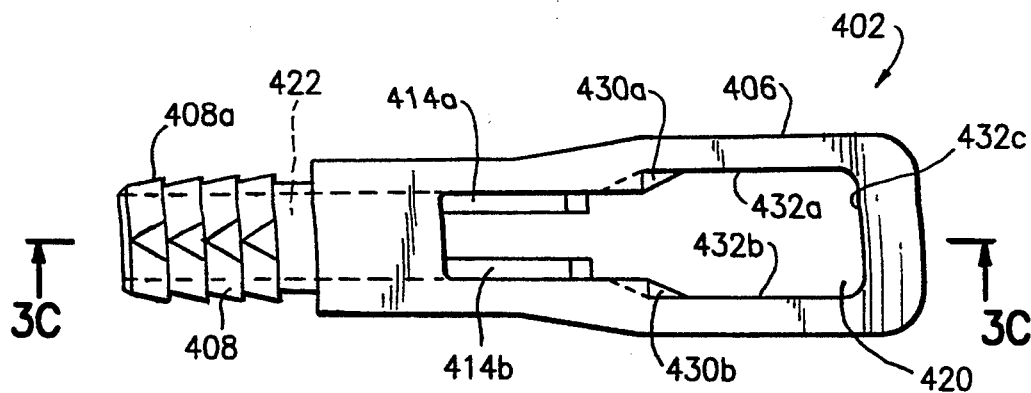
FIG. 3a is a top view of the stationary end effector jaw.

FIGS. 3a–3i show further details of the stationary jaw 402. The shank portion 408 of the stationary jaw 402 is narrower than the distal portion 406 and is provided with ribs 408a for engaging the interior of tube 15 (FIG. 1). The distal portion 406 is provided with an opening 420 defined by walls 432a, 432b, 432c. As seen best in FIGS. 3h and 3i, walls 432a and 432b have an outer taper such that they terminate in sharp upper edges 433a, 433b (wall 432c also being tapered and terminating in sharp upper edge 433c). In this manner a scissor like action is provided (as will be described in more detail below) when the sharp upper edges 433a, 433b engage the knife-like edges 416 of the movable jaw as the movable jaw is moved from the open to the closed position (FIGS. 2a and 2b). As seen in FIG. 3a, the walls 432a, 432b also narrow as they extend in the proximal direction due to tapered recesses 430a, 430b which engage tapered shoulders of the movable jaw 404 as described below. Between the head and shank portions of stationary jaw 402, there are provided arcuate flanges 414a, 414b which engage arcuate grooves 412a, 412b of the movable jaw 404. A channel 422 (U-shaped or otherwise) extends through the shank portion 408 to the opening 620 for receiving push rod 60 as shown in FIGS. 2a and 2b.

Figure 3B:
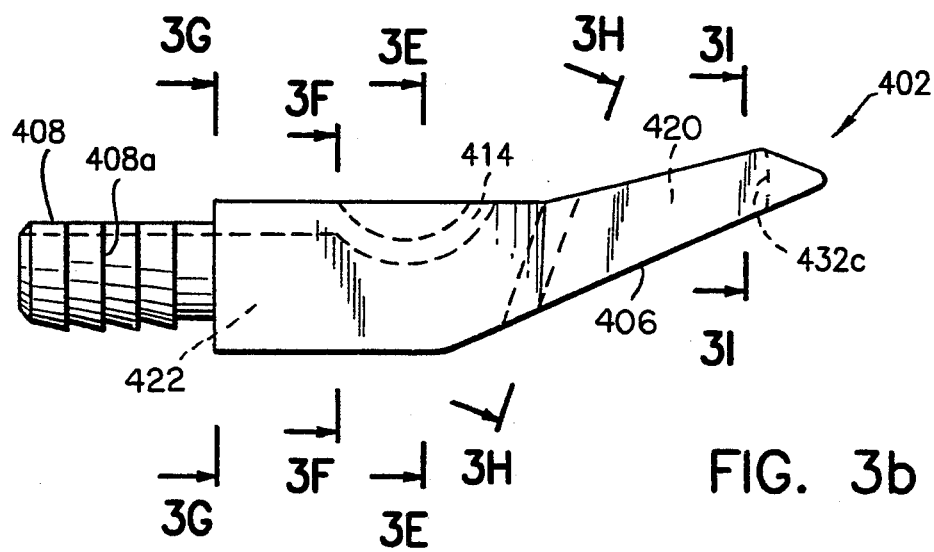
FIG. 3b is a side view of the stationary end effector jaw.
Figure 3C:
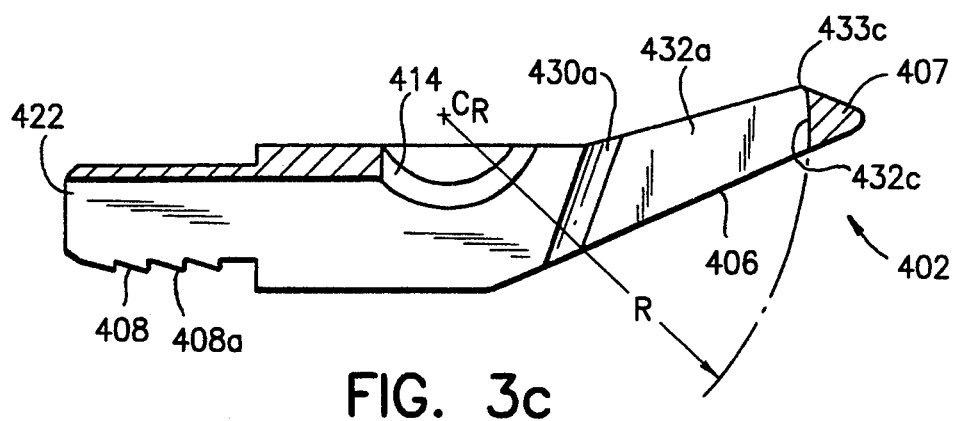
Figure 3D:
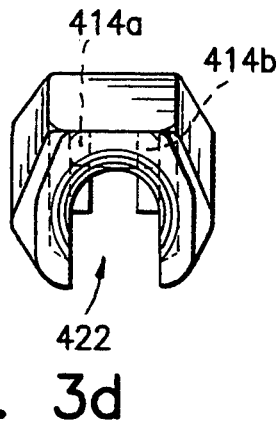
FIG. 3d is a proximal end view of the stationary jaw end effector.
Figure 3E:
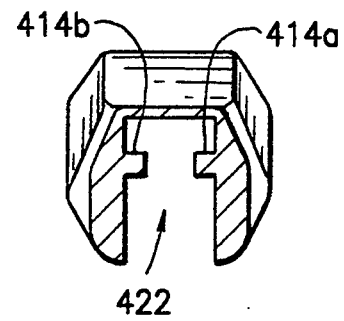
FIGS. 3e-3i are cross sectional views respectively along lines 3E—3E, 3F—3F, 3G—3G, 3H—3H, and 3I—3I in FIG. 3b.
Figure 3F:
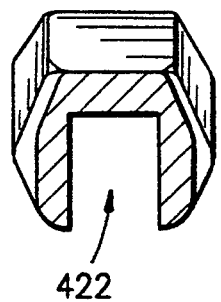
Figure 3G:
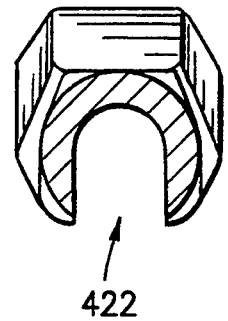
Figure 3H:
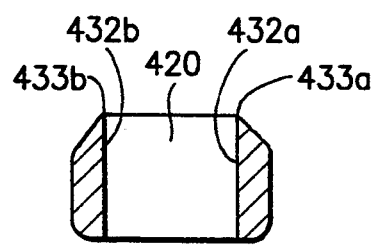
Figure 3I:
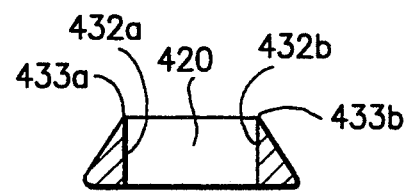

As seen best in FIGS. 3b and 3c, the distal portion 406 of the stationary jaw 402 is angled by about fifteen degrees relative to the shank portion 408. It will be appreciated, however, that the invention also applies to arthroscopic tools where the end effectors are angled differently relative to the tube 15 or not angled at all.

Also seen in FIGS. 3b and 3c is a distal nose 407 which terminates at proximal opening defining wall 432c. According to a preferred aspect of the invention, the wall 432c, which helps define opening 420, is concave. The concavity of wall 432c is defined by a radius R from the axis of rotation CR of the movable jaw 404 as seen in FIG. 3c, and further helps in the cutting action as described in more detail below.

As seen best in FIGS. 3d–3g, the entire bottom of the channel 422 is open to better accommodate the push rod 60 as shown in FIGS. 2a and 2b. It will be appreciated, however, that if desired, the insulating shrink wrap 20 could extend over at least a portion of that opening.

Turning now to FIGS. 4a through 4f, the movable jaw 404 is shown in greater detail. The movable jaw 404 has a shank portion 426 and a distal portion 436. The shank portion is somewhat narrower than the distal portion and includes arcuate grooves 412a, 412b, for mating with arcuate flanges 414a, 414b of the stationary jaw 402, and a throughbore 418 for receiving push rod pin 430 (FIGS. 2a and 2b). The distal portion 436 is somewhat broader than the shank portion but small enough to fit inside opening 420 of stationary jaw 402. The distal portion is provided with knife-like edges 416a, 416b and is joined to the shank portion 426 by tapered shoulders 428a, 428b. It will be appreciated, however, that the invention also applies to arthroscopic tools where the shank portion is provided with a width which is the same as, or wider than the distal portion.

Figure 4A:
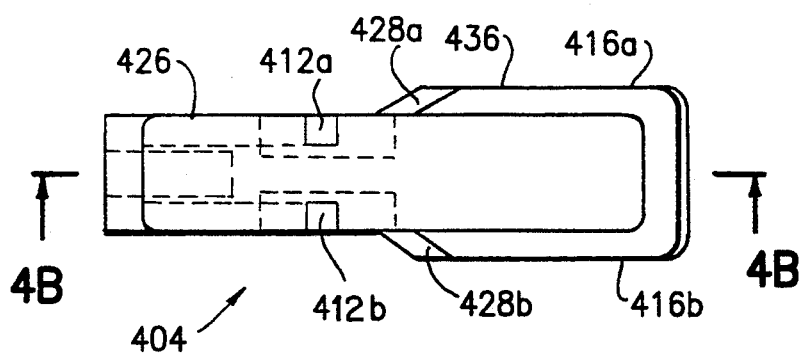
FIG. 4a is a top view of the movable jaw end effector.
Figure 4B:
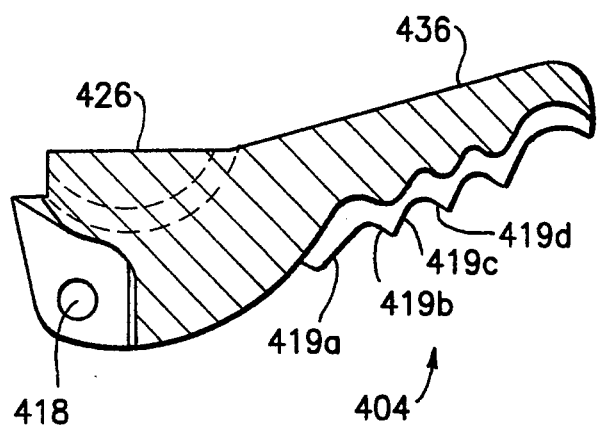
Figure 4C:
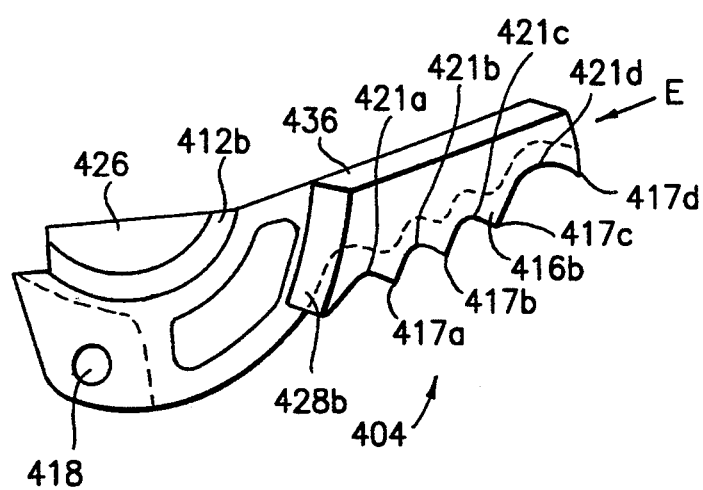
FIG. 4c is a side elevation view of the movable jaw end effector.
Figure 4D:
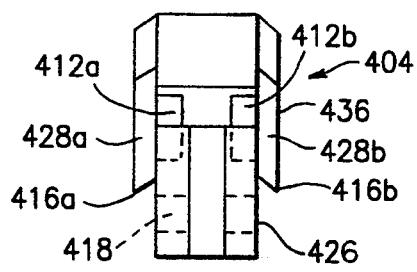
FIG. 4d is a proximal end view of the movable jaw end effector.
Figure 4E:
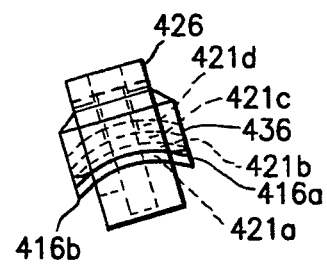
FIG. 4e is a distal end view of the movable jaw end effector looking in the direction E in FIG. 4c.
Figure 4F:
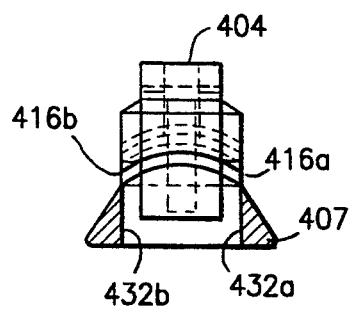
FIG. 4f is a a composite end view in partial section of the distal end of the movable and stationary jaws.

As seen best in FIGS. 4b and 4c, the knife-like edges 416a, 416b of the movable jaw 404 comprise a plurality of serrations 419a, 419b, 419c... The serrations effectively define teeth, e.g. 417a–417d, and wells, e.g. 421a–421d between the teeth. As seen in FIGS. 4b and 4c, the serrations are cut at angles of approximately ninety degrees relative to each other (with well 421a actually defining a one hundred four degree angle, and wells 421b and 421c defining ninety degree angles in the preferred embodiment), although hooked serrations (such as well 421d) with a radius could also be utilized. According to a preferred aspect of the invention, both the teeth 417a–417d and the wells 421a–421d are concave between edges 416a and 416b as seen best in FIG. 4e. It will be appreciated that with the concavity of the teeth 417a–417d and wells 421a–421d of the movable jaw 404 (which define knife-like serrated edges 416a, 416b), and with the sharp upper edges 433a, 433b of the opening defining walls 432a, 432b of the stationary jaw 402, the cutting action that results when the movable jaw is rotated into the opening 430 of the stationary jaw is (double) scissor-like (see FIG. 4f) with two sets of two sharp surfaces contacting each other.

With the teeth being concave, it will be appreciated that at the distal end of the arthroscopic instrument, the cutting edges 416a and 416b of the most distal tooth 417d will contact the sharp upper edges 433a, 433b of the stationary jaw 402 prior to the remainder of concave tooth 417d contacting sharp upper edge 433c. However, as the movable jaw 404 continues to close, cutting will continue along the concave tooth 417d and the upper edge 433c of wall 432c. This cutting is enhanced due to the fact that the nose portion 407 of the stationary jaw 402 has the concave wall 432c. The concave wall 432c prevents material from wedging between the wall 432c and the distal tooth 417d as the distal concave tooth 417d continues to rotate into opening 420.

According to another aspect of the invention, the concave teeth and wells in the movable jaw 404 are formed with the wells being deep enough such that a "back-cutting" effect is obtained. In particular, as the movable jaw 404 closes in the stationary jaw 402, the apex of the teeth 417 in the knife-like edges 416a, 416b of the movable jaw 404 contact the sharp upper cutting edges 433a, 433b of the stationary jaw before points just proximal the apex (as seen at 499 of FIG. 2c). In other words, as the jaws close, at first a single cutting point is established which moves distally along the well. Prior to the cutting point reaching the nadir of the well, the next distal cutting tooth 417 engages the cutting edges 433a, 433b, and two cutting contact points are established. The first cutting contact point is the continuation of the distally moving point. The second cutting point moves proximally down the proximal side of the next distal cutting tooth to the nadir of the well. It is this second cutting point which occurs due to the depth and angle of the teeth which effects the back-cutting.

Figure 5A:
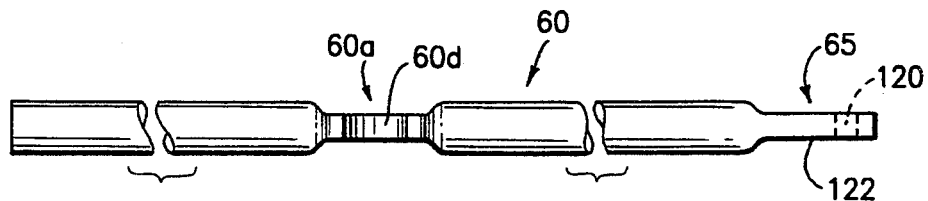
FIG. 5a is a broken top view of the push rod.
Figure 5B:
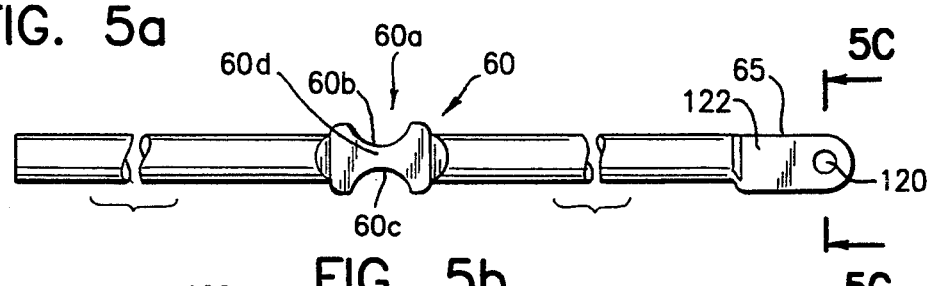
FIG. 5b is a broken side view of the push rod.
Figure 5C:
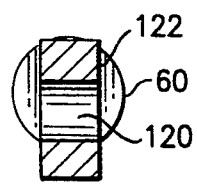
FIG. 5c is an enlarged cross sectional view along line 5C—5C in FIG. 5b.
Figure 5D:
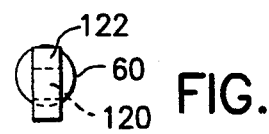
FIG. 5d is a distal end view of the push rod.

FIGS. 5a-5d show a preferred embodiment of push rod 60 for use with the arthroscopic surgical instrument according to the invention. The distal end 65 of the cylindrical push rod is provided with a flattened plate like terminal portion 122 which may be swaged from the longitudinal axis of push rod 60 as shown in FIG. 5b. This terminal portion 122 is also provided with one or more through holes 120 for engaging an end effector as described above. In accord with the invention, push rod 60 is further provided with a weakened frangible portion 60a which, as shown in FIGS. 5a and 5b, is a flattened portion with substantially semicircular side cuts 60b, 60c. The substantially semicircular side cuts in the flattened portion of the push rod allow for substantial tolerance in manufacturing and result in a more consistent frangible link. The side cuts 60b, 60c are dimensioned so that the continuity of push rod 60 depends on a frangible link portion 60d. It will be appreciated that the strength and thus frangibility of portion 60d of push rod 60 can be specifically adjusted according to the thickness of flattened portion 60a and the size of side cuts 60b, 60c. In accord with the invention, the frangible link portion should have a tensile strength such that it will break before an end effector or distal linkage breaks. In furtherance of this object, the push rod 60 is ideally constructed of Carpenter Technologies Custom 455 stainless steel solution treated to an ultimate tensile strength of −150,000/180,000 psi with a hardness of RC 33-37. The push rod is then age hardened at 1000 degrees F for two hours and air cooled in a protective atmosphere to an ultimate tensile strength of 210,000/250,000 psi with a hardness of RC 44-50. The diameter of push rod 60 is typically 0.061 inches. Flattened frangible portion 60a will have a typical thickness of approximately 0.030 inches and a height of approximately 0.010 inches thereby extending slightly beyond the diameter of push rod 60. Side cuts 60b, 60c are typically semicircular cuts having a radius of approximately 0.04 inches each leaving the frangible link portion 60d with a minimum height of approximately 0.002 inches. The flattened plate like terminal portion 122 of distal end 65 of the push rod 60 typically has a thickness of approximately 0.030 inches, a height of approximately 0.061 inches and is offset from the longitudinal axis of the push rod by approximately 0.009 inches. The through hole 120 typically has a diameter of approximately 0.033 inches and is centered 0.021 inches from the distal end of portion 122. With the provided dimensions and materials, the push rod has a tensile strength of approximately one hundred and ten pounds.

As will be appreciated from the above description, axial movement of the push rod 60 causes the jaws to open and close. Moreover, the weakest link in the operation of the jaws is the frangible link 60d of the push rod. Thus, when cutting hard bone tissue, should too much force be applied through the push rod, the frangible link will break before any portion of the end effector breaks, thereby preventing the accidental deposit of foreign material in the incised joint.

There has been described and illustrated herein an arthroscopic surgical instrument. While particular embodiments of the invention have been described, it is not intended that the invention be limited thereto, as it is intended that the invention be as broad in scope as the art will allow and that the specification be read likewise. Thus, while particular end effectors have been disclosed, it will be appreciated that other end effectors could be utilized with the frangible link and cautery aspects of the invention. Moreover, while the scissor-like punch end effector is shown with the movable jaw having arcuate grooves and the stationary jaw having arcuate flanges, it will be appreciate that the flanges and grooves may be interchanged, or that other mechanisms utilized and the same results obtained. Also, while particular linkage means have been shown, it will be recognized that other types of linkage means could be used to couple the push rod with the end effector with similar results obtained. Further, while specific details as to the jaws of the arthroscopic tool of the invention were provided, it will be appreciated that changes may be made thereto, e.g., in the number and angles of the teeth, etc. Similarly, while particular design dimensions and materials were disclosed with regard to the frangible link and other arthroscopic instrument elements, it will be appreciated that other dimensions and materials could be utilized. It will therefore be appreciated by those skilled in the art that yet other modifications could be made to the provided invention without deviating from its spirit and scope as so claimed.

What is claimed is:

1. An arthroscopic surgical instrument, comprising:
   a) a hollow tube having a proximal and a distal end;
   b) a stationary jaw coupled to said distal end of said hollow tube;
   c) a movable jaw which rotates relative to said stationary jaw;
   d) actuating means coupled to said movable jaw for moving said movable jaw, said actuating means coupled to said proximal end of said hollow tube, wherein said stationary jaw is provided with a pair of spaced apart side walls defining an opening for receiving said movable jaw, each of said side walls having an inner surface and an outer surface which meet at a first sharp edge defined by an acute angle between said inner surface and said outer surface, and said movable jaw is provided with a pair of spaced apart second sharp edges with a concave inner surface between said second sharp edges, wherein when said movable jaw is rotated relative to said stationary jaw, said first sharp edges and second sharp edges effect a scissor-like cutting action.

2. An arthroscopic surgical instrument according to claim 1, wherein:
said outer surfaces of said side walls of said stationary jaw are tapered.

3. An arthroscopic surgical instrument according to claim 2, wherein:
said side walls of said stationary jaw are substantially triangular in cross section.

4. An arthroscopic surgical instrument according to claim 1, wherein:
said movable jaw rotates about an axis of rotation, and
said stationary jaw has a distal wall further defining said opening, said distal wall having an inner surface having a concavity defined by a radius from said axis of rotation.

5. An arthroscopic surgical instrument according to claim 4, wherein:
said distal wall is tapered.

6. An arthroscopic surgical instrument according to claim 1, wherein:
each of said second sharp edges of said movable jaw are serrated to form teeth and wells, where the teeth and wells of a first of the second sharp edges are coupled by said concave inner surface to the teeth and wells of a second of said second sharp edges.

7. An arthroscopic surgical instrument according to claim 6, wherein:
said stationary jaw has a distal wall further defining said opening, and said distal wall and a distal of said teeth in conjunction with said concave inner surface coupling said distal of said teeth forming a cutting edge.

8. An arthroscopic surgical instrument according to claim 7, wherein:
said movable jaw rotates about an axis of rotation, and
said distal wall of said stationary jaw has an inner surface having a concavity defined by a radius from said axis of rotation.

9. An arthroscopic surgical instrument according to claim 6, wherein:
said first sharp edges lie along a plane, and
said wells are cut sufficiently deeply such that an apex of at least one tooth of said teeth reaches said plane before a surface of said tooth proximal said apex reaches said plane, thereby effecting back-cutting.

10. An arthroscopic surgical instrument according to claim 6, wherein:
at least one of said teeth is hook-shaped.

11. An arthroscopic surgical instrument according to claim 6, wherein:
at least one of said teeth is triangular and forms an approximately ninety degree angle.

12. An arthroscopic surgical instrument according to claim 1, wherein:
said actuating means comprises a lever coupled to a push rod, said push rod being coupled to said movable jaw and having an integral frangible link.

13. An arthroscopic surgical instrument according to claim 12, wherein:
said frangible link comprises a flattened portion of said push rod with a pair of substantially semicircular side cuts in said flattened portion.

14. An arthroscopic surgical instrument according to claim 1, further comprising:
electrical connector means extending through a non-conductive portion of said actuation means and coupled to said hollow tube, said electrical connector means for supplying a cautery current via said hollow tube to said stationary jaw; and
insulation means for covering an outer surface of said hollow tube.

15. An arthroscopic surgical instrument, comprising:
a) a hollow tube having a proximal and a distal end;
b) a stationary jaw coupled to said distal end of said hollow tube;
c) a movable jaw which pivots relative to said stationary jaw;
d) actuating means coupled to said movable jaw for moving said movable jaw, said actuating means also being coupled to said proximal end of said hollow tube and having a non-conductive portion;
e) electrical connector means extending through said non-conductive portion of said actuating means and coupled to said hollow tube for supplying a cautery current via said hollow tube to said stationary jaw; and
f) insulation means for covering an outer surface of said hollow tube.

16. An arthroscopic surgical instrument according to claim 15, wherein:
said actuating means comprises a non-conductive lever and a push rod, said push rod being coupled to said movable jaw.

17. An arthroscopic surgical instrument, comprising:
a) a hollow tube having a proximal and a distal end;
b) end effector means of a first strength coupled to said distal end of said hollow tube;
c) actuating means coupled to said hollow tube for actuating said end effector means, said actuating means including a lever and a substantially cylindrical push rod having a longitudinal axis with said push rod coupled to said lever and having a frangible link portion which is flattened substantially parallel to the longitudinal axis of the push rod and includes a pair of strength reducing side cuts, and said push rod further comprising coupling means of a second strength for coupling said push rod to said end effector means, wherein said frangible link has a third strength which is weaker then said first and second strengths, such that application of a force applied to said end effector means by said actuating means via said push rod causes said frangible link portion of said push rod to break prior to either one of said end effector means and said coupling means breaking.

18. An arthroscopic surgical instrument according to claim 17, wherein:
said side cuts are substantially semicircular.

19. An arthroscopic surgical instrument according to claim 18, wherein:

said end effector means comprises a stationary jaw coupled to said distal end of said hollow tube, and a movable jaw coupled to said coupling means and pivoting relative to said stationary jaw.

20. An arthroscopic surgical instrument according to claim 19, wherein:
   said stationary jaw is provided with a first arcuate engaging surface for engaging said movable jaw,
   said movable jaw is provided with a second arcuate engaging surface for engaging said first arcuate engaging surface,
   said stationary jaw is provided with a throughbore for receiving said push rod, and
   said coupling means comprises a pin which couples said movable jaw to said push rod.

21. An arthroscopic surgical instrument, comprising:
   a) a hollow tube having a proximal and a distal end;
   b) a stationary jaw coupled to said distal end of said tube, said stationary jaw having a pair of side walls and a distal end wall defining an opening, said distal end wall having a concave inner surface;
   c) a movable jaw coupled to said actuating means and pivoting about an axis of rotation relative to said stationary jaw, wherein said movable jaw pivots in said opening, and said concave inner surface of said distal end wall is defined by a radius from said axis of rotation, with a distal portion of said movable jaw closely engaging said concave inner surface when said movable jaw pivots in said opening; and
   d) actuating means coupled to said proximal end of said tube and coupled to said movable jaw for effecting pivoting of said movable jaw relative to said stationary jaw.

22. An arthroscopic surgical instrument according to claim 21, wherein:
   said actuating means comprises a lever and a push rod coupled to said lever and to said movable jaw such that movement of said lever results in movement of said said push rod which in turn results in movement of said movable jaw about said axis of rotation.

* * * * *